(12) United States Patent
Hays et al.

(10) Patent No.: US 7,581,874 B2
(45) Date of Patent: Sep. 1, 2009

(54) APPARATUSES AND SYSTEMS FOR MONITORING FOULING OF AQUEOUS SYSTEMS INCLUDING ENHANCED HEAT EXCHANGER TUBES

(76) Inventors: George F. Hays, 99 Skyline Dr., Morristown, NJ (US) 07960; Eric P. Hoernle, 39 Fox Hill Rd., Lafayette, NJ (US) 07848

( * ) Notice: Subject to any disclaimer, the term of this patent is extended or adjusted under 35 U.S.C. 154(b) by 0 days.

(21) Appl. No.: 11/393,943

(22) Filed: Mar. 31, 2006

(65) Prior Publication Data

US 2007/0025413 A1 Feb. 1, 2007

Related U.S. Application Data

(60) Provisional application No. 60/666,750, filed on Mar. 31, 2005.

(51) Int. Cl.
*G01N 25/72* (2006.01)
*G01N 25/40* (2006.01)
*G01K 7/02* (2006.01)

(52) U.S. Cl. .............................. 374/7; 374/147; 374/45; 374/5; 374/29; 374/179

(58) Field of Classification Search ............... 374/4, 374/5, 7, 43, 44, 165, 57, 147, 148, 137, 374/29, 39, 45, 6, 112, 100, 166, 179; 702/33–35; 73/592; 252/964, 960
See application file for complete search history.

(56) References Cited

U.S. PATENT DOCUMENTS

| | | | | |
|---|---|---|---|---|
| 2,831,951 A | * | 4/1958 | Desloge | 338/241 |
| 3,222,916 A | * | 12/1965 | Davis | 374/54 |
| 3,306,109 A | * | 2/1967 | Caparone | 428/616 |
| 3,918,300 A | * | 11/1975 | Weisstuch et al. | 73/112 |
| 4,138,878 A | * | 2/1979 | Holmes et al. | 374/7 |
| 4,358,957 A | * | 11/1982 | Lougheed et al. | 374/134 |
| 4,383,438 A | * | 5/1983 | Eaton | 73/61.62 |
| 4,686,854 A | | 8/1987 | Herman | |

(Continued)

FOREIGN PATENT DOCUMENTS

WO WO 03/031347 4/2003

(Continued)

OTHER PUBLICATIONS

Webb et al., "Fouling in Enhanced Tubes Using Cooling Tower Water Part 1: Long-Term Fouling Data", International Journal of Heat and Mass Transfer, No. 43, 2000, pp. 3567-3578.

(Continued)

*Primary Examiner*—Gail Verbitsky
(74) *Attorney, Agent, or Firm*—David L. Hedden

(57) ABSTRACT

Heat transfer test assemblies for monitoring and recording fouling of aqueous systems are disclosed. The heat transfer test assemblies include an outer tube member, a heating rod positioned within the outer tube member, a ribbed tube sleeve fitted over the heating rod and thermocouples for sensing the wall temperature of heating rod. The disclosed heat transfer test assemblies enable improved monitoring of systems employing enhanced heat exchanger tubes. Monitoring and recording apparatuses including the heat transfer test assemblies are also disclosed.

5 Claims, 8 Drawing Sheets

U.S. PATENT DOCUMENTS

| | | | | |
|---|---|---|---|---|
| 4,718,774 | A * | 1/1988 | Slough | 374/7 |
| 4,722,610 | A * | 2/1988 | Levert et al. | 374/43 |
| 5,178,009 | A * | 1/1993 | Arekapudi et al. | 73/292 |
| 5,254,310 | A * | 10/1993 | Bressan | 422/53 |
| 5,353,653 | A * | 10/1994 | Watanabe et al. | 73/865.9 |
| 5,460,041 | A * | 10/1995 | Andes et al. | 73/335.08 |
| 5,576,481 | A | 11/1996 | Beardwood et al. | |
| 5,611,920 | A | 3/1997 | Simpson | |
| 5,615,733 | A * | 4/1997 | Yang | 165/11.1 |
| 6,054,678 | A | 4/2000 | Miyazaki | 219/237 |
| 6,062,069 | A * | 5/2000 | Panchal et al. | 73/53.01 |
| 6,068,012 | A | 5/2000 | Beardwood et al. | |
| 6,284,144 | B1 | 9/2001 | Itzhak | |
| 6,325,535 | B1 * | 12/2001 | Gibson et al. | 374/29 |
| 6,386,272 | B1 * | 5/2002 | Starner et al. | 165/11.1 |
| 6,499,876 | B1 * | 12/2002 | Baginksi et al. | 374/7 |
| 6,715,914 | B1 * | 4/2004 | Fesmire et al. | 374/45 |
| 6,840,251 | B2 | 1/2005 | Gill | |
| 6,840,261 | B2 | 1/2005 | Gill | |
| 6,959,588 | B2 * | 11/2005 | Zougari et al. | 73/61.62 |
| 7,192,187 | B2 * | 3/2007 | Blichmann | 374/147 |
| 7,249,885 | B2 * | 7/2007 | Van Den Ende et al. | 374/147 |
| 2004/0013563 | A1 | 1/2004 | Romer | |
| 2005/0013878 | A1 | 1/2005 | Mingzhong | |
| 2008/0163692 | A1 * | 7/2008 | Huang et al. | 73/627 |

FOREIGN PATENT DOCUMENTS

| | | |
|---|---|---|
| WO | WO 2004/026770 | 4/2004 |
| WO | WO 2005/019117 | 3/2005 |

OTHER PUBLICATIONS

Li et al., "Fouling Characteristics of Internal Helical-Rib Roughness Tubes Using Low-Velocity Cooling Tower Water", International Journal of Heat and Mass Transfer, No. 45, 2002, pp. 1685-1691.

Li et al., "Fouling In Enhanced Tubes Using Cooling Tower Water Part II: Combined Particulate and Precipitation Fouling", International Journal of Heat and Mass Transfer, No. 43, 2000, pp. 3579-3588.

Beardwood et al, "Implications of Various Dispersants on Biofilm Clean Up Processes", Corrosion 99, No. 301, 1999, pp. 1-26.

Beardwood et al., "Detection and Reduction of Biofilms in Industrial Cooling Waters", 1999 International Water Conference 99-71, pp. 1-22.

Beardwood, "Development of Performance-Based Control Technology for Cooling Water Treatment", International Water Conference 02-29, pp. 1-15.

Ashland Drew Industrial, "Controlled Fouling/Scaling In Cooling Waters", Technical Bulletin, RS-1090-CTB, pp. 1-15.

Trevor V. Suslow, "Oxidation-Reduction Potential (ORP) for Water Disinfection Monitoring, Control, and Documentation", UC Davis Div. of Ag. and Nat. Resources, Pub #8149.

* cited by examiner

APPARATUSES AND SYSTEMS FOR MONITORING FOULING OF AQUEOUS SYSTEMS INCLUDING ENHANCED HEAT EXCHANGER TUBES

This application claims the benefit of U.S. provisional application No. 60/666,750, filed on Mar. 31, 2005 and entitled Heat Transfer Test Assembly for an Apparatus for Monitoring Fouling of Aqueous Systems, the entire disclosure of which is incorporated herein by reference.

BACKGROUND

The chemical water treatment industry has historically been involved with reducing or inhibiting the inherent scale forming or fouling tendencies of natural waters associated with large industrial cooling water systems. Many of the foulant components found in water systems originate with the incoming supply, but some contaminants enter the system from the local environment or from process contamination.

Fouling is an extremely complex phenomenon. Fouling of a heat transfer surface is defined as the deposition on a surface of any material which increased the resistance to heat transfer. The fouling tendency of a fluid in contact with a heat transfer surface is a function of many variables including the components of the fluid, which in the case of water include, inter alia, crystals, silt, corrosion products, biological growths, process contaminates, etc. Generally, foulant deposits comprise a combination of several of these materials in relationship to, among other things, the geometry of the heat transfer surface, materials of construction, temperature, etc.

If the fouling tendency of a cooling water system can be accurately predicted before a plant is designed and built, significant capital savings might be realized through more accurate heat exchanger specifications. It is a normal practice to design a heat exchanger with increased heat exchanger surface area to overcome losses in performance caused by fouling deposits with such additional surface area often accounting for more than twenty percent of the actual surface area of the heat exchanger. When such design practice is employed with titanium, stainless steel and similar expensive materials of construction, it can be appreciated that capital expenditures might be significantly reduced if data could be developed to anticipate and provide for an anti-foulant protocol.

U.S. Pat. Nos. 4,339,945 ('945), Re. 33,346 (Re. '346), U.S. Pat. Nos. 4,346,587 (Re. '587) and Re. 33,468 (Re. '468), the entire disclosures of which are incorporated by reference, disclose a mobile apparatus for monitoring and evaluating fouling tendencies of fluids, such as fluid in a cooling water system. The mobile apparatus includes a heat transfer test assembly and related conduit and valve assemblies for connection in fluid flow communication to a heat transfer apparatus for in-situ fouling testing of the fluid passing therethrough, and further includes a monitoring and recording apparatus. The heat transfer test assembly includes a heating rod coaxially positioned within a transparent tubular member for controlled heat input. The heating rod includes a tube member surrounding an insulating matrix in which a heating element is embedded. The test assembly further includes thermocouples to measure the wall temperature of the heating member to permit fouling determinations at varying flow rates with simultaneous monitoring and recording thereof together with data, such as corrosion, pH, conductivity, and the like. The fouling tendency of a fluid may be evaluated by the passage of a fluid through the heat transfer test assembly under controlled rates of flow and heat output from the heating element through measurement of temperature drops between the tube member and the fluid to permit a determination of the resistance of the scale formation therefor. The apparatuses covered by the '945, Re. '346, '587 and Re. '468 patents are marketed by Drew Chemical of Ashland Inc. as the P-U-L-S-E (sm) analyzer.

Current cooling water systems commonly employ heat exchangers having tubes with enhanced heat exchange surfaces (internal and external). Heat exchanger tubes with "enhanced" external surfaces often have external fins to promote more efficient heat exchange, particularly where the external surface is exposed to a condensing refrigerant. Heat exchanger tubes with "enhanced" internal surfaces have internal helical flutes similar to rifling in a gun barrel, particularly where the internal surface is exposed to an aqueous cooling medium. Such enhancements, and particularly internal flutes, promote the precipitation of solids from an aqueous stream and provide an ideal environment for the growth of biomass. In fairly short order, the flutes may become fouled with a biomass rich foulant layer to such an extent that most or all of the benefits of the tube enhancement become neutralized.

Internally enhanced tubes have been found to biofoul at significantly faster rates and to a greater degree than smooth bore tubes. Conversely, smooth bore tubes experience inorganic precipitation/crystallization fouling at a faster rate than internally enhanced tubes. The apparatuses and methods disclosed in the '945, Re. '346, '587 and Re. '468 are effective in accurately evaluating fouling tendencies of fluids in systems using smooth heat exchanger tubes. However, enhanced heat exchanger tubes tend to biofoul faster and to a greater degree than testing using the test apparatuses and methods described in the '945, Re '346, '587 and Re '468 patents will indicate.

In view of the above, there remains a need for an improved apparatus for monitoring fouling in aqueous systems using enhanced heat exchanger tubes. Particularly, there is a need for an apparatus that allows for more rapid detection of biofouling in aqueous systems employing enhanced heat exchanger tubes. Additionally, there is a need for a monitoring system that allows for direct, rapid detection of fouling of enhanced heat exchanger tubes as well as smooth heat exchanger tubes.

BRIEF SUMMARY

Although it is known in the industry that enhanced (i.e., non-smooth bore) heat exchanger tubes are more prone to fouling than smooth-bore heat exchanger tubes, the present inventors have noted some surprising discoveries with regard to fouling of smooth-bore and enhanced heat exchanger tubes. Particularly, the present inventors have discovered that:

1) inorganic precipitation/crystallization fouling occurs at a faster rate on smooth bore heat exchanger tubes compared to enhanced heat exchanger tubes of the same material (i.e., enhanced tubes are less susceptible to inorganic scaling); and 2) microbiological fouling and subsequent suspended solids entrapment by the biological foulant occur far more rapidly on enhanced heat exchanger tubes than smooth-bore tubes of the same material.

Knowing that biofouling occurs more rapidly on non-smooth surfaces than on smooth surfaces, the present inventors have realized that biofouling in an aqueous system including enhanced heat exchanger tubes could be detected more quickly if the heater rod of a heat transfer test assembly such as the '945 patent and '587 patent test assemblies, which have a smooth outer surface, were provided with an element having a non-smooth (i.e., enhanced) surface for collecting biofilm, wherein the enhanced surface is the inner surface of the annular test conduit. In aqueous systems having heat exchanger tubes with non-smooth ("enhanced") inner bores, earlier detection of biofouling could allow one to determine biofilm formation prior to excessive build-up of biofilm on the heat exchanger tubes. The inventors further recognized that using an enhanced rod as the inner surface of the annular test conduit provides a less confining environment for modeling than the actual heat exchanger tube with its internal enhancements. In addition, using an enhanced rod as the inner surface of the annular test conduit provides the advantage of being able to visually observe the deposition and cleaning process.

In order to achieve the above objectives, heat transfer test assemblies for apparatuses for monitoring and recording fouling of aqueous systems are provided. Monitoring and recording apparatuses including a novel heat transfer test assemblies according to the embodiments described below are also disclosed.

According to one embodiment disclosed herein, a heat transfer test assembly for an apparatus for monitoring and recording fouling of aqueous systems is provided, wherein the heat transfer test assembly comprises:

an outer tube member;
a heating rod positioned coaxially within the outer tube member, said heating rod comprising means for sensing a wall temperature of said heating rod;
a ribbed tube sleeve coaxially fitted over the heating rod within the outer tube member; and
an annular fluid flow passageway disposed between the tube sleeve and the outer tube member.

According to another embodiment disclosed herein, a heat transfer test assembly for an apparatus for monitoring and recording fouling of aqueous systems comprises:

an outer tube member;
a heating rod positioned coaxially within the outer tube member, said heating rod comprising means for sensing a wall temperature of said heating rod;
a tube sleeve assembly coaxially fitted over the heating rod within the outer tube member, wherein said tube sleeve assembly comprises a ribbed sleeve section, an upstream flow transition section positioned upstream of and butted against an upstream end of the ribbed sleeve section, and a downstream flow transition section positioned downstream of and butted against a downstream end of the ribbed sleeve section; and
an annular fluid flow passageway disposed between the tube sleeve assembly and the outer tube member.

A test assembly including an enhanced rod as described above incorporated in a side stream heat transfer test section can be utilized to detect fouling occurrence rapidly as well as tracking the clean-up improvements to completion. This capability can provide enhancements to performance-based monitoring control for cooling waters. If used in conjunction with a smooth bore tube monitor (i.e., a monitor with a smooth rod as disclosed in U.S. Pat. Nos. 4,339,945, Re. 33,346, 4,346,587 and Re. 33,468) in parallel, an enhanced tube monitor (i.e., a monitor with an enhanced rod) can allow for categorization of the type of foulant that is detected. Thus, the appropriate mitigation method and chemistry selection can be implemented.

The monitoring capabilities of systems employing the disclosed enhanced tube test assembly promote rapid foulant detection and characterization, and allow for proactive corrective treatment measures that can prevent excessive heat transfer losses and the development of localized corrosion. This monitoring and foulant control technology should allow for a broader acceptance and applicability of the use of enhanced heat exchanger tubes in the cooling water industry. Although the devices and systems described herein are generally described in the context of an aqueous heat transfer fluid circulating through a heat exchanger, it will be understood that the devices and systems are applicable to any heat transfer fluid including hydrocarbons, euthetic salt solutions and the like, circulating through a vessel in heat transfer relationship where fouling is a problem.

Additional features and advantages will become apparent from the following description and drawings.

BRIEF DESCRIPTION OF THE DRAWINGS

FIG. 9 is a schematic diagram of a process and apparatus for continuously testing, monitoring and recording data relative to the heat transfer test assembly as well as for monitoring and recording data related to corrosion, conductivity, pH and the like.

DETAILED DESCRIPTION

Figure 1:
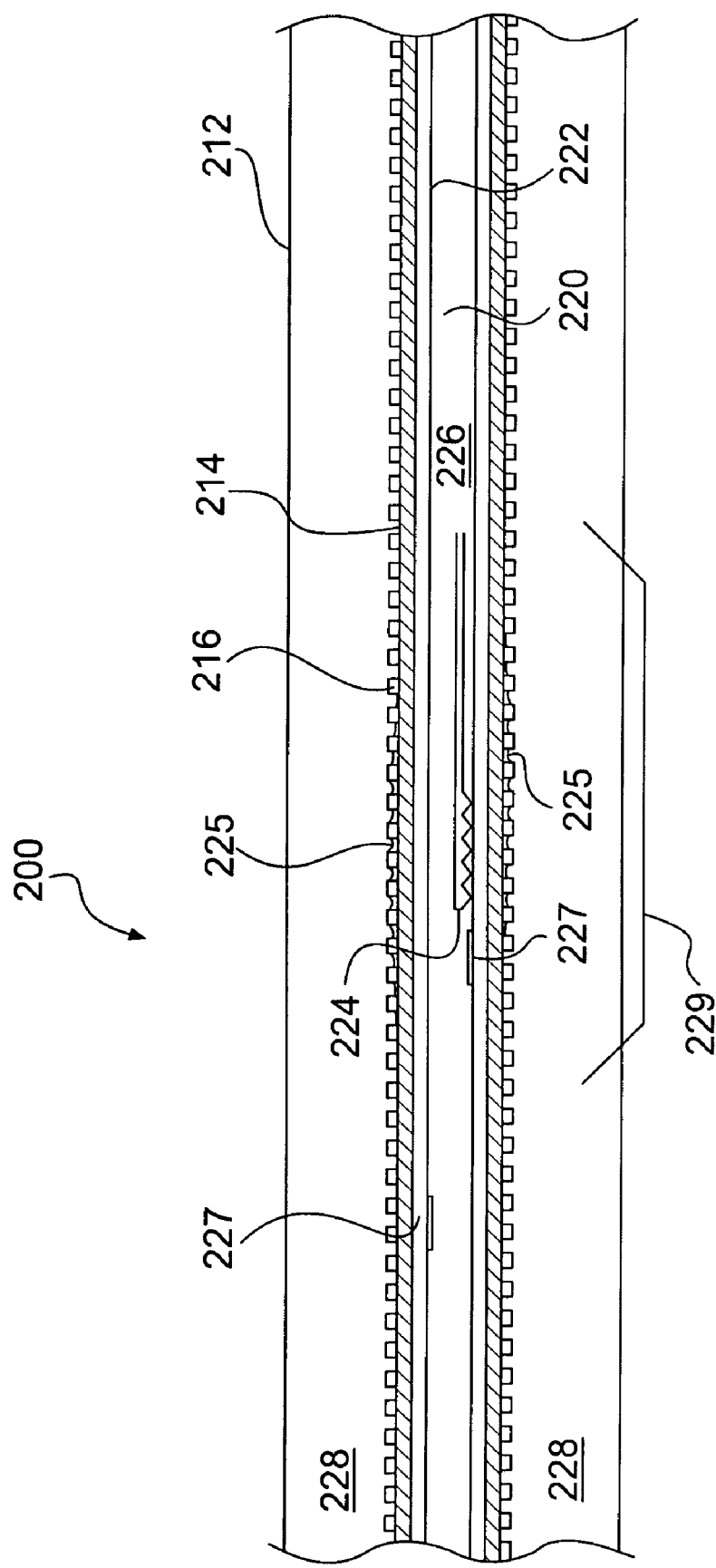
FIG. 1 is a cross-sectional elevational view of a heat transfer test assembly according to one embodiment.
Figure 2:
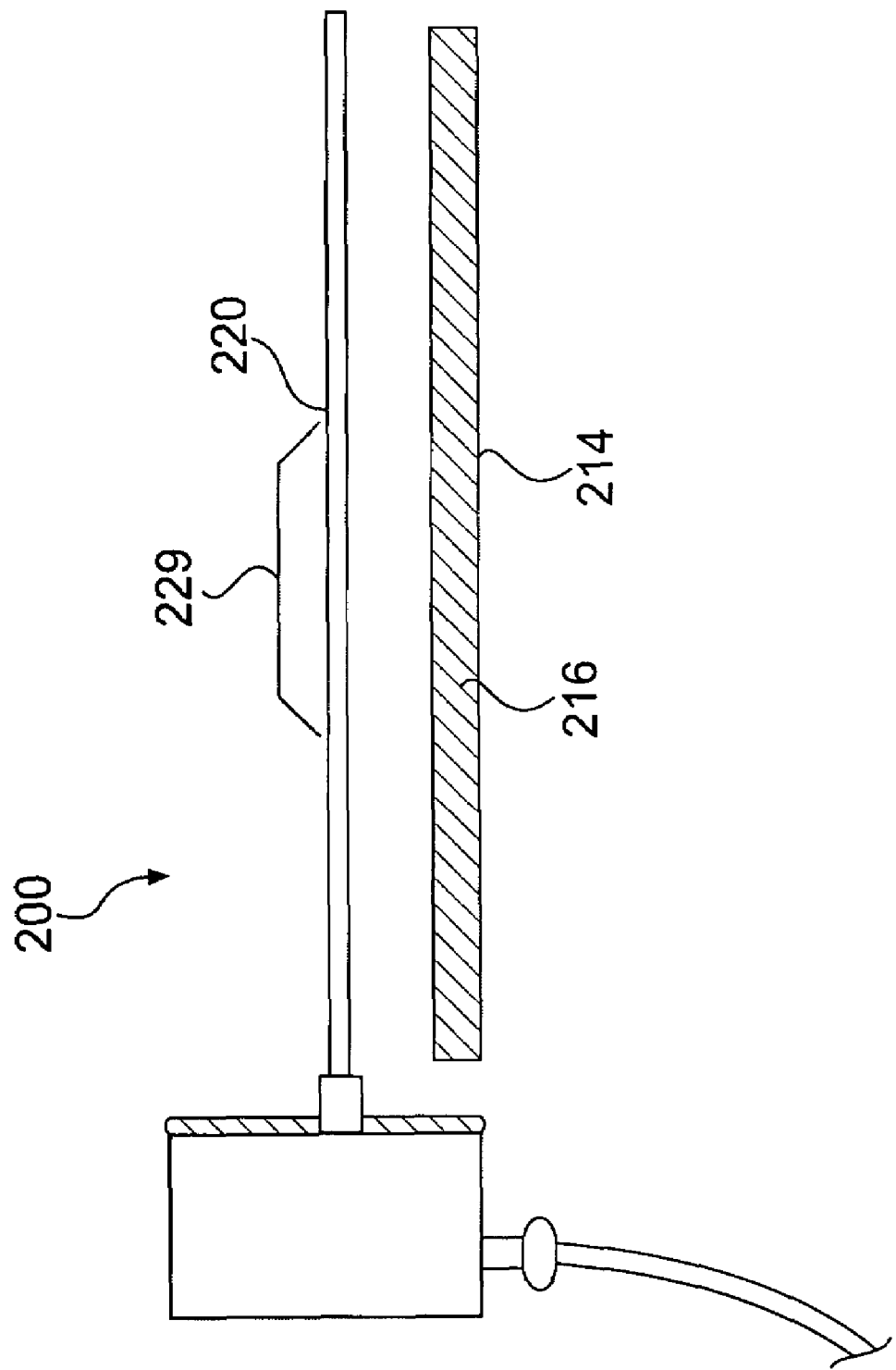
FIG. 2 is a perspective view showing the components of the heat transfer test assembly of FIG. 1 in a disassembled state.

Referring to FIGS. 1 and 2, there is illustrated a heat transfer test assembly according to one embodiment, generally indicated as 200. The assembly 200 generally comprises a transparent outer tube member 212, a ribbed tube sleeve 214 coaxially positioned within the tube member 212, and a cylindrically-shaped heating rod 220 positioned coaxially within the tube sleeve 214. In other words, the tube sleeve 214 is fitted over the heating rod 220 within the tube member 212. The heating rod 220 is formed of a tubular member 222 in which a heating element 224 is embedded within an insulating matrix 226, such as magnesium oxide. The heating rod 220 and tube sleeve 214 are coaxially positioned within the tube member 212 to form an annular fluid flow passageway 228 between the tube sleeve 214 and the tube member 212. Symmetrically disposed in the tubular member 222 of the heating rod 220 is a plurality of surface thermocouples 227 generally disposed at positions corresponding to the hour hand at 3, 6, 9 and 12 o'clock for sensing the wall temperature of the tubular member 222 in the same cross-sectional plane.

The tube member 212 is formed of any suitable transparent material, such as glass, to permit visual observation of flow as well as foulant formation 225 about the surface of the heating rod 214. The tube member 222 of the heating rod 220 is formed of a metallic material, such as stainless steel, copper, titanium, mild steel, admiralty metal or the like, dependent on the fluid to be initially tested by passage through the test assembly 200, or in the case of existing units of a like metallic material as that in the unit. Normally, stainless steel is used for normal cooling water application whereas admiralty metal is employed for sea water and brackish water applications. The tube sleeve 214 is preferably formed of copper or copper alloy, but may be formed of another metallic material, such as stainless steel, titanium, mild steel, admiralty metal or the like, dependent on the fluid to be initially tested by passage through the test assembly 200, or in the case of existing units of a like metallic material as that in the unit. For testing of enhanced heat exchanger tubes, the heater rod 222 and enhanced sleeve 214 should be constructed of the same metallurgy to prevent galvanic corrosion.

The tube sleeve 214 includes a plurality of helical ribs 216 on an outside surface thereof, preferably extending at least over an area of the sleeve 214 that surrounds the heated section 229 of the heating rod 220. According to one embodiment, the heated section 229 is approximately 5.5 inches long, and the helical ribs 216 correspondingly extend around a 5.5 inch long section of the sleeve 214. However, the ribs 216 may extend over the entire length of the sleeve 214. The heating rod 220 and tube sleeve 214 may be jointly referred to as an "enhanced rod," based on the provision of ribs or enhancements to the outside surface of the tube sleeve 214.

Figure 8:
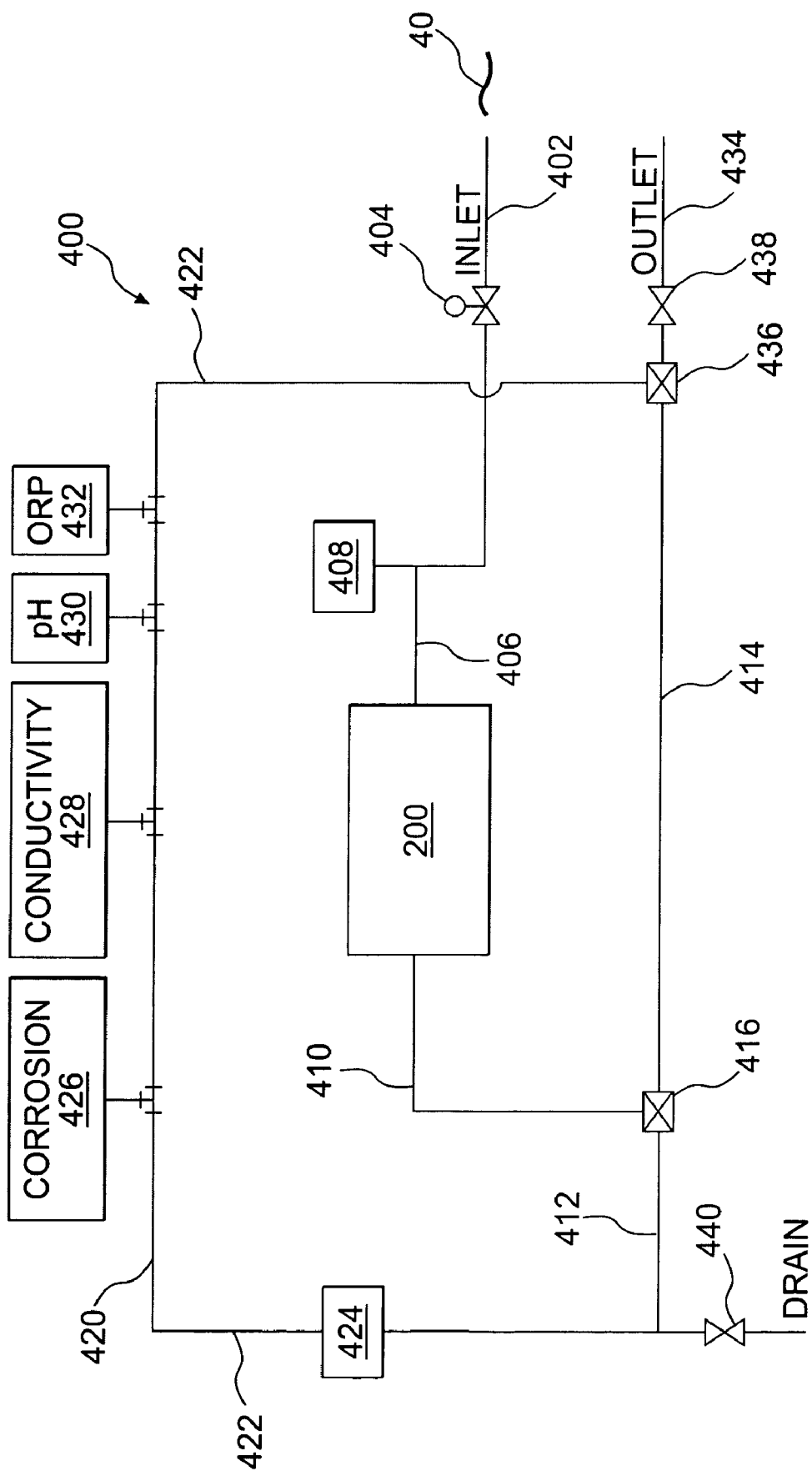
FIG. 8 is a piping diagram of an apparatus including the heat transfer test assembly.
Figure 9:
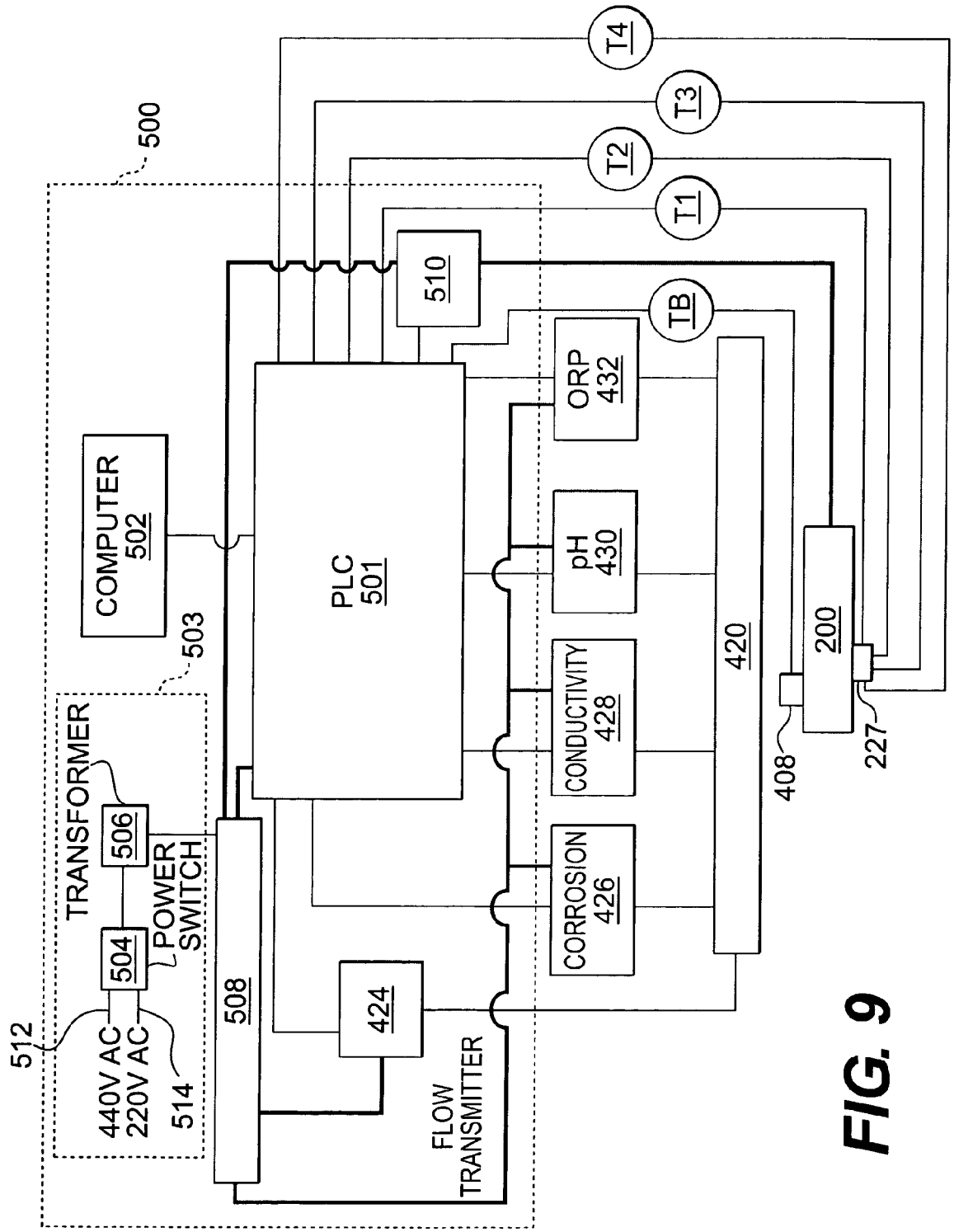

As more fully hereinafter described, the fouling tendency of a fluid may be evaluated by the passage of a fluid through the heat transfer test assembly 200 under controlled rates of flow and heat output from the heating element 224 through measurement of temperature drops ($\Delta$ts) between the tube sleeve 214 and the fluid to permit a determination of the resistance (R) of the foulant formation 225 therefor. Referring to FIG. 8, the heat transfer test assembly 200 is positioned within a piping assembly 400. The piping assembly 400 may be integrated or coupled with a monitoring and recording assembly 500, as shown in FIG. 9, including components of the piping assembly disposed on a support structure (not shown) for positioning within a mobile container (not shown), such as a trailer, van or the like, for ease of movement from location to location to test a fluid passing through a unit such as a heat exchanger reactor or the like. The container may include environment capabilities to provide pre-select conditions of temperature, humidity and the like to insure proper functioning of the various units of the monitoring and recording assembly 500.

FIG. 8 illustrates the piping assembly 400 including the heat transfer test assembly 200. In order to provide sufficient range of flow velocities, a plurality of heat transfer test assemblies 200 of differing diameters may be used for interchangeable insertion of the piping assembly 400.

The piping assembly 400 includes an inlet conduit 402 controlled in fluid flow communication with a test assembly inlet conduit 406 under the control of a motorized inlet valve 404. The valve 404 may be a proportional integral derivative (PID) type valve to insure flow at a preselected value. A bulk fluid thermocouple 408 is provided at the test assembly inlet conduit 406 for monitoring the temperature of the fluid entering the inlet conduit 402. The piping assembly further includes a test assembly outlet conduit 410 which is selectably in fluid flow communication with a conduit 412 leading to a flow cell 420 or a bypass conduit 414 leading under the control of a 3-way bypass valve 416. The flow cell 420 includes a conduit 422 and a paddle wheel flow transmitter 424, a corrosion sensor 426, a conductivity sensor 428, a pH sensor 430 and an oxidation-reduction-potential sensor (ORP) 432 connected to the conduit 422 by a plurality of probes. The exit end of the conduit 422 is selectively in fluid communication with the piping assembly outlet conduit 434 under the influence of a three-way valve 436. The bypass conduit 414 is also in selective fluid flow communication with the outlet conduit 434 under the control of the valve 436 to allow fluid to bypass the flow cell 420 when necessary. Fluid entering the outlet conduit 434 is discharged from the piping assembly 400 back to the system being monitored under the control of isolation valve 438. Excess fluid remaining in the piping assembly 400 following operation may be drained from conduits 412 and 422 via drain valve 440.

FIG. 9 shows a monitoring and recording assembly 500 which may include or be connected to the piping assembly 400. The monitoring and recording assembly 500 includes a programmable logic controller (PLC) 501 and a personal computer (PC) 502. A power inlet assembly 503 for powering the PLC 501 and the monitors 426, 428, 430 and 432 includes a $440V_{ac}$ inlet connector 512 and a $220V_{ac}$ inlet connector 514 connected to a transformer 506 through a power switch 504. The transformer 506 provides isolated 220 volt power to an electrical distributor 508, which distributes power to separately to the PLC 501, monitors 424, 426, 428, 430 and 432 and a solid-state power controller 510. The switch 504 automatically allows only one of the inlet connectors 512, 514 to supply power at a given time.

The solid-state power controller 510 supplies power to the heating rod 220 of the test assembly 200. The power controller 510 further generates a power level signal representative of the power level of the heating element 220 and transmits the power level signal to an analog-to-digital converter (not shown) of the PLC 501.

Thermocouples 227 and 408 generate temperature signals $T_1$-$T_4$ and $T_B$, respectively, and transmit the temperature signals to a thermocouple module (not shown) within the PLC 501. The measurement of the temperature drop between the wall of the tube sleeve 214 and the fluid ($\Delta$ts, discussed above) is measured by the readings of signals $T_1$, $T_2$, $T_3$ and $T_4$ of wall thermocouples 227 versus the reading of signal $T_B$ of bulk water thermocouple 408. The flow transmitter 424 generates an analog signal representative of fluid flow rate in the flow cell 420 and transmits the signal to an analog module (not shown) within the PLC 501. The flow transmitter 424, corrosion sensor 426, conductivity sensor 428, pH sensor 430 and ORP sensor 432 are connected to the analog module (not shown) of the PLC 501 and thereby transmit analog signals to the PLC 501.

As is known in the art, the PLC 501 provides a PID control signal for the flow control valve 404 and separately provides a PID signal for the solid state power controller 510. Additionally, the PLC 501 records and stores sets of time-stamped data. These data are transmitted to the computer 502 for recording in a referenced time frame. The computer may be connected via modem or network (not shown) to transmit the data to remote sites.

In operation, the monitoring and recording assembly 500 is placed on a suitable support assembly and enclosed in a self-contained environmental container, and is caused to be positioned adjacent a unit operation or process such as a heat exchanger or delignification digester, respectively, employing a fluid to be tested, inter alia, for fouling tendencies to permit evaluation and develop an antifoulant protocol. A source of power is connected to the power inlet assembly 503 and a flexible conduit 40 is placed in fluid flow communication with the unit operation or process, generally on the up-stream side thereof. As shown in FIG. 8, the circulating fluid is caused to flow via conduit 40 into the piping assembly 400 by control of valve 404, and then sequentially through the test assembly 200 via conduit 406, out of the test assembly 200 and through the flow cell 420 via conduit 412. The fluid is thereafter discharged out of the outlet conduit 434 to waste, or to the unit operation or process.

During operation, power is supplied to the heating element 224 of the test assembly 200, with the temperature of the tubular member 222 being monitored by taking measurements at each of the four wall thermocouples 227. An average fouling factor is calculated based on the measurements taken at the four wall thermocouples 227. One of the wall thermocouples 227 is used to monitor the temperature of the heating rod 220 for a high temperature cutoff function, which cuts off power to the heating element 224 for safety in the event that the temperature of the heating rod 220 becomes too high. Simultaneously, the bulk fluid temperature is monitored by thermocouple 408 together with the monitoring of the fluid velocity by flow transmitter 424 to determine what, if any, velocity effects there are on fouling under given operating conditions. Water velocity is controlled by the flow control valve 404.

As stated above, the wall thermocouples 227 and the bulk water temperature thermocouple 408 are connected to the analog-converter (not shown) of the PLC 501 to convert analog electrical signals to digital output signals which are transmitted for recordation to the computer printer, it being understood that the computer printer is capable of effecting some computation to generate calculated data, such as a u-coefficient and/or fouling factor. Such fouling factor is time related to data from the ORP sensor 426, the conductivity sensor 428, the pH monitor 430 and the corrosion monitor 432. In this manner, various data are simultaneously collected of factors relating to fouling, etc. with corrective anti-foulant action taken if dictated by the recorded data.

Prior to or during a testing operation, a bypass mode of the piping assembly 400 may be used to allow an operator to check and/or adjust the calibration of the flow transmitter 424 and sensors 426, 428, 430 and 432 without stopping fluid flow through the test assembly 200. Thus, the integrity of any fouling deposit on the heating rod 220 of the test assembly 200 can be maintained during equipment calibration. In bypass mode, fluid enters the inlet conduit 402, flows through the conduit 406 and the test assembly 200, then exits the test assembly 200 through conduit 410, and thereafter flows through the bypass conduit 414 and out of the outlet conduit 434. The bypass mode is primarily used for extended fouling runs, such as fouling runs extending beyond 30 to 60 days. Mobile monitoring and recording assemblies will rarely employ the bypass operation, as such assemblies are generally used for shorter runs of 14 to 45 days.

After recording the aforementioned data, the piping assembly 400 is disconnected from the unit operation or process by closing valves 404, 438 and 440, and disconnecting the conduit 40 from the fluid source. Thereafter, the monitoring and recording assembly 500 and piping assembly 400 may be easily moved to another location within the plant or to another plant site.

According to alternative embodiments, the heat transfer test assembly 200 may be incorporated in a piping assembly and/or monitoring and recording assembly such as those described in U.S. Pat. Nos. 4,339,945 ('945), Re. 33,346 (Re. '346), U.S. Pat. Nos. 4,346,587 and Re. 33,468 (Re. '468), the entire disclosures of which are incorporated herein by reference.

Figure 3:
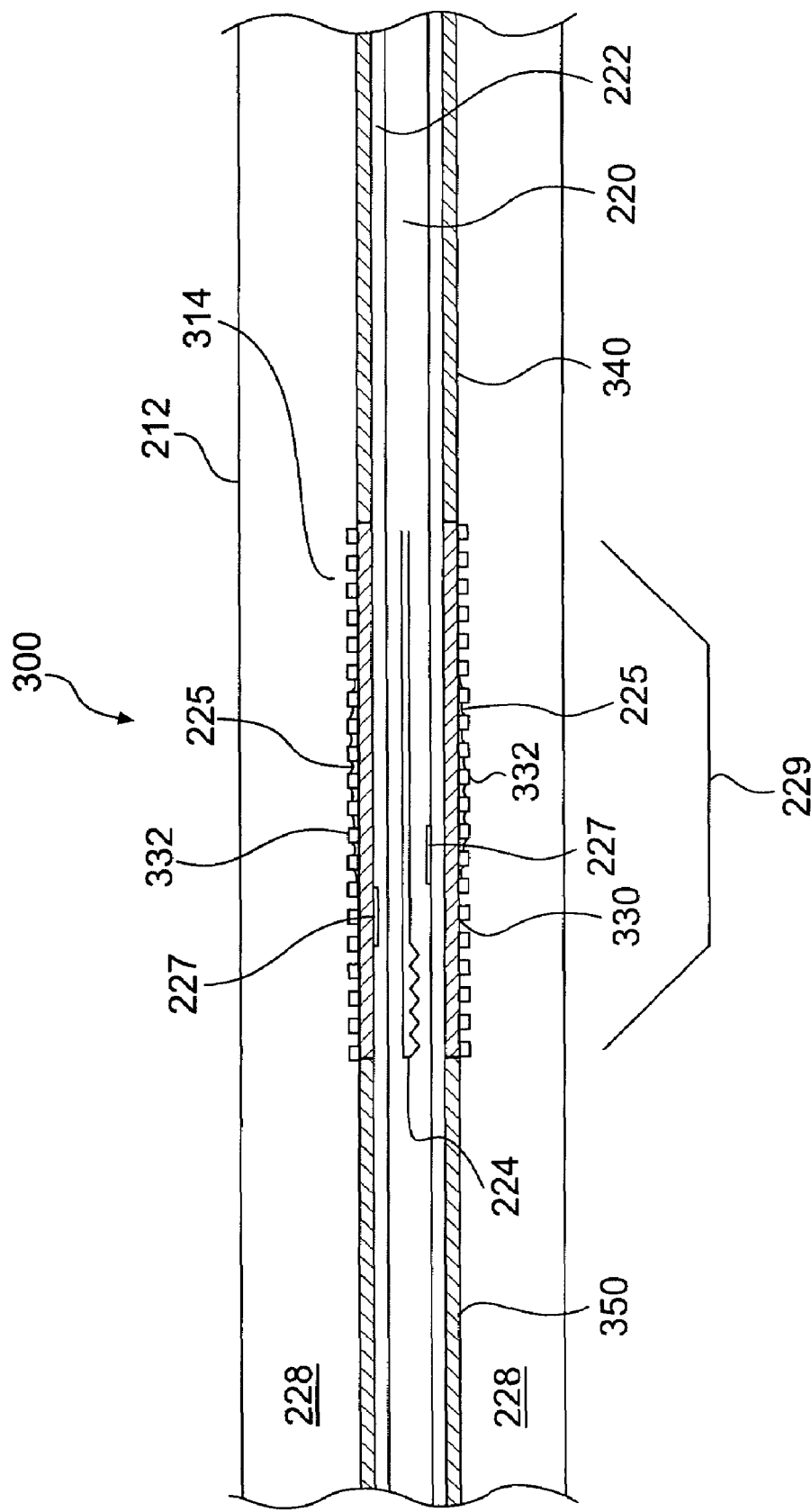
FIG. 3 is a cross-sectional elevational view of a heat transfer test assembly according to another embodiment.
Figure 4B:
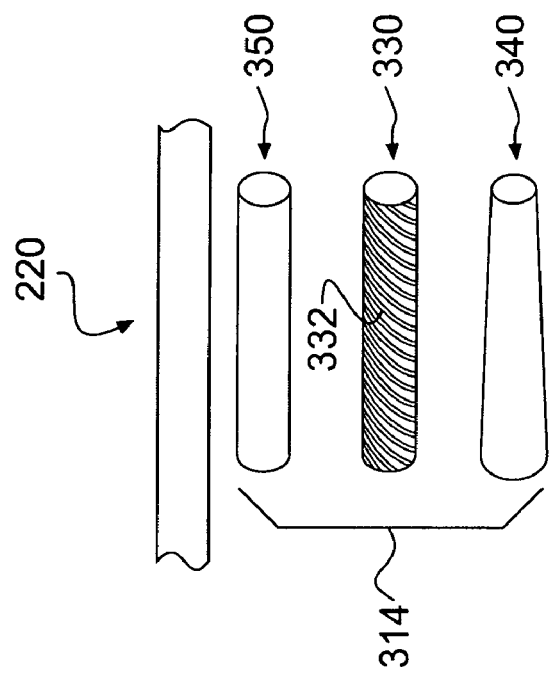
FIGS. 4A-4C are perspective views showing the components of the heat transfer test assembly of FIG. 3 in a disassembled state.
Figure 4A:
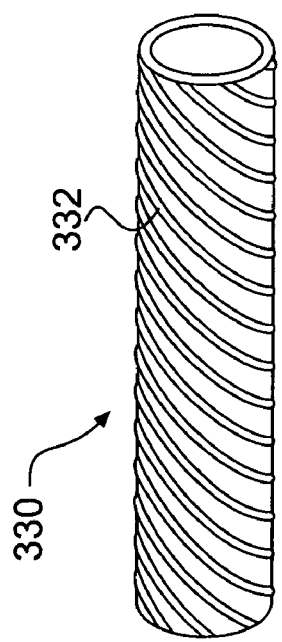
Figure 4C:
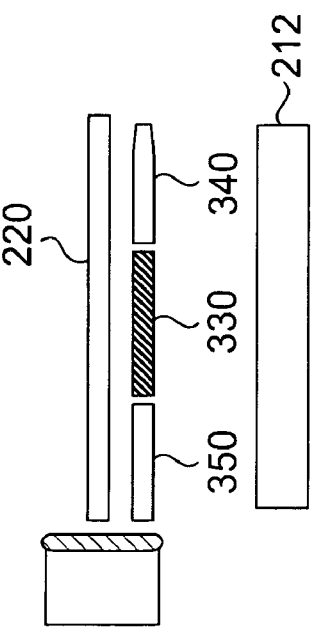

Another embodiment of a heat transfer test assembly, indicated by reference numeral 300, is shown in FIGS. 3-4C. The assembly 300 is similar to the assembly 200, except that the assembly 300 includes a tube sleeve assembly 314 in place of the tube sleeve 214. As shown in FIGS. 3-4C, the tube sleeve assembly 314 includes three separate sections: an enhanced, ribbed sleeve section 330; an upstream flow transition section 340 positioned upstream of and butted against an upstream end of the ribbed sleeve section 330; and a downstream flow transition section 350 positioned downstream of and butted against a downstream end of the enhanced sleeve section 330.

The ribbed sleeve section 330 includes helical ribs 332 on an exterior surface thereof, and preferably is situated over and has a length substantially equal to the length of the heated section 229 of the heating rod 220. The flow transition sections 340 and 350, which have smooth outer surfaces, minimize transition turbulence of the fluid flowing over the sleeve assembly 314. The upstream flow transition section 340 is preferably tapered from a smaller outer diameter to a larger outer diameter from its upstream end to its downstream end. The outer diameter of the downstream end of the upstream flow transition section 340 and the outer diameter of the upstream end of the downstream flow transition section 350 preferably match the base outer diameter (i.e., the diameter to the base of the ribs 332) of the enhanced sleeve section 330 to provide smooth fluid flow characteristics. The heating rod 220 and the tube sleeve assembly 314 may be jointly referred to as an enhanced rod.

The tube sleeve assembly 314 is more cost effective to manufacture and easier to install over the heating rod 220 than the unitary sleeve 214. The heating rod 220, according to certain embodiments, may be about 22 inches (56 cm) long. The rod 220 may not be entirely straight and may bend or flex under its own weight or during use. Therefore, it may, in certain instances, be difficult to fit the unitary tube sleeve 214 over the heating rod 220. Additionally, it is more costly and difficult to manufacture the tube sleeve 214 with a consistent bore over such a long length. By providing three separate sections, the tube sleeve assembly 314 is easier to manufacture and install.

According to certain embodiments, a tube sleeve 214 or enhanced sleeve section 330 may include ribs 216 or 332 having the following properties:

| | |
|---|---|
| Helix angle ($\alpha$): | 29.3 degrees |
| Rib height (e): | 0.0113 inches (0.0287 cm) |
| Rib axial pitch (P): | 0.234 |
| Number of starts ($n_s$): | 31 |
| P/e value: | 20.7 |
| Tube diameter to top of rib (De): | 0.527 inches (1.339 cm) |
| e/De value: | 0.021 |

The outer surface of the tube sleeve 214 or sleeve section 330 will biofoul at a faster rate than it would if it were a smooth surface. The fouling potential of the sleeve 214 or sleeve section 330 increases as $n_s$ increases ($n_s$ is the number of flutes or grooves between adjacent ribs), wherein $n_s \geq 30$ are more susceptible to fouling. The fouling potential of the sleeve 214 or sleeve section 330 also increases as the helix angle ($\alpha$) increases, wherein value of $\alpha \geq 35$ degrees is more susceptible to biofouling. Additionally, fouling potential increases as the rib axial pitch (P) to rib height (e) ratio decreases, specifically wherein ratios of P/e 4.0 are more susceptible to biofouling. Furthermore, fouling susceptibility increases with lower rib height (e) to base tube diameter (De) (i.e., diameter to the base of a rib).

The enhanced fouling tendencies of the tube sleeve 214 and tube sleeve assembly 314 are provided by lower velocity recirculating zones in the axial regions between the ribs 216, 332. These zones cause higher drag which results in lower surface shear stress. Thus, the ribbed sleeve 214 or sleeve section 330 increases the foulant deposit rate, and the drag profile associated with the ribs 216, 332 does not contribute to the deposit removal process.

The advantages of the disclosed apparatuses and systems are exhibited in the following experimental examples:

EXAMPLES

A test rig was adapted to have two test heat exchanger sections run in parallel in the same cooling system. One test section was equipped with an enhanced tube sleeve assembly (with helical ribs) as described in the embodiment of FIGS. 3-4C. The enhanced section of the tube sleeve assembly had the following characteristics:

| | |
|---|---|
| Helix angle (α): | 29.3 degrees |
| Rib height (e): | 0.0113 inches (0.0287 cm) |
| Rib axial pitch (P): | 0.234 |
| Number of starts ($n_s$): | 31 |
| P/e value: | 20.7 |
| Tube diameter to top of rib (De): | 0.527 inches (1.339 cm) |
| e/De value: | 0.021 |

The other test section used a standard heating rod (i.e., heating rod 220 without an enhanced tube sleeve/tube sleeve assembly). From this point forward, for the sake of simplicity, the test section with the enhanced tube sleeve assembly and the test section without the tube sleeve assembly will be referred to as the "enhanced rod" and "smooth rod," respectively. The test protocol called for both tubes to be of the same copper metallurgy and to emulate the same tube-side flow conditions, which were a velocity of 5 ft/s (1.6 m/s) and a surface temperature of 95-100° F. (35-37.8° C.). Initially, a baseline test was run with city water that was not permitted to concentrate. This test was performed to prove that the protocol was properly constructed. Subsequent tests were run with city water that was naturally concentrated by the system to a level of 5 cycles of concentration.

The test rig consisted of a cooling tower, a circulating pump, a small water to water heat exchanger, which is used to supply a heat load to allow the tower water to concentrate, and a laboratory version of Ashland's P-U-L-S-E (sm) analyzer, which consists of three parallel independent heat transfer test sections. The system had an operating volume of 0.22 m³ (58 gallons), a cold water temperature of 33° C. (92° F.) and a temperature drop of 2.8° C. (5° F.) across the cooling tower. Maximum circulation was 76 L/m (20 gpm). During these tests, a portion of the circulating water was bypassed to the tower basin to maintain the cold water temperature (temperature drop across the cooling tower with the limited heat input). The system was automated. The concentration of circulating water was maintained by conductivity control. In addition, fouling factor, pH and ORP were constantly monitored. See Table 1 for the operating conditions and design of the test rig.

TABLE 1

Pilot Cooling Tower Test Rig Operating Design Conditions

| | |
|---|---|
| System Volume | 0.22 m³ (58 gallons) |
| Recirculation Rate | 4.542 m³/hr (20 gpm) |
| Volume to Recirculation Ratio | 3:1 |
| Cooling Tower Temperature Drop (ΔT) | 2.8° C. (5° F.) |
| Cooling Water Apparent Retention Time in Test Rig | Approximately 22 to 23 hours |
| Standard Uncycled Make-up Water Chemistry | |
| Calcium, mg/L as $CaCO_3$ | 81 |
| Magnesium mg/L as $CaCO_3$ | 48 |
| Total Alkalinity, mg/L as $CaCO_3$ | 96 |

TABLE 1-continued

| | |
|---|---|
| Bicarbonate Alkalinity, mg/L as $CaCO_3$ | 96 |
| Chloride mg/L as Cl | 58 |
| Sulfate, mg/L as $SO_4$ | 46 |
| pH | 7.4 |

Example 1

Inorganic Fouling

Figure 5:
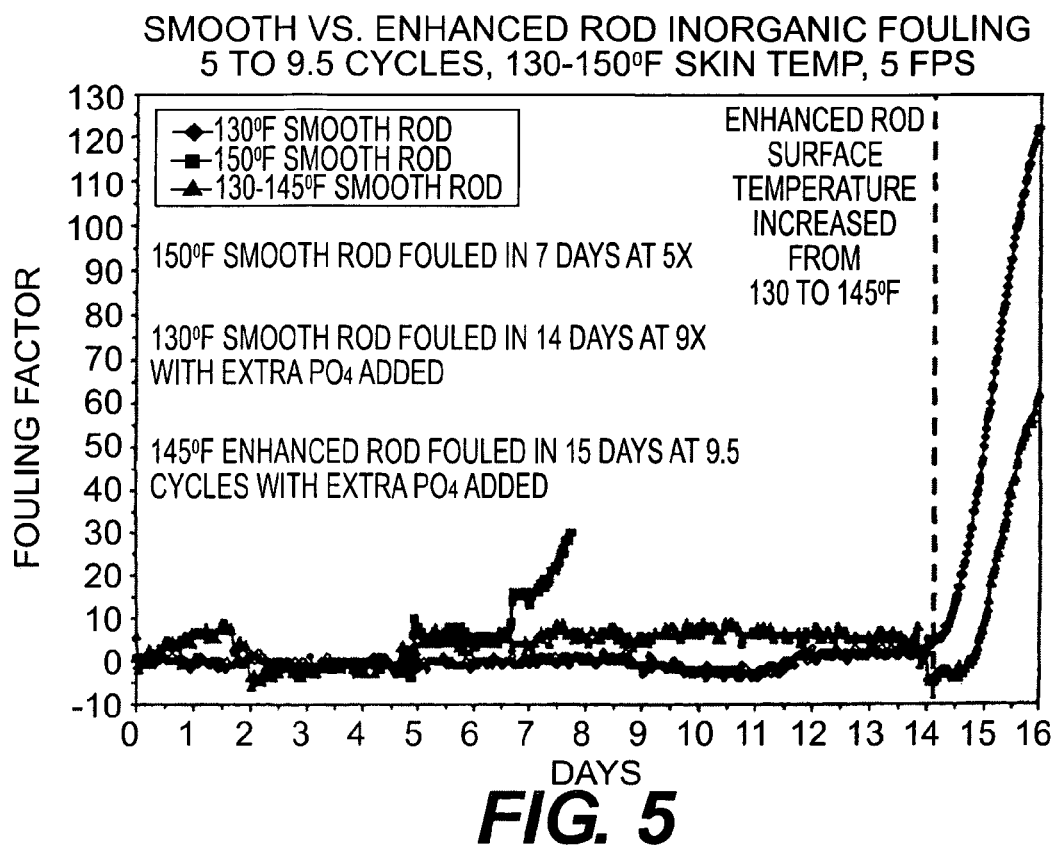
FIGS. 5-7 are plots showing experimental fouling data for a heat transfer test assembly with a smooth rod and a heat transfer test assembly with an enhanced rod under various conditions.
Figure 6:
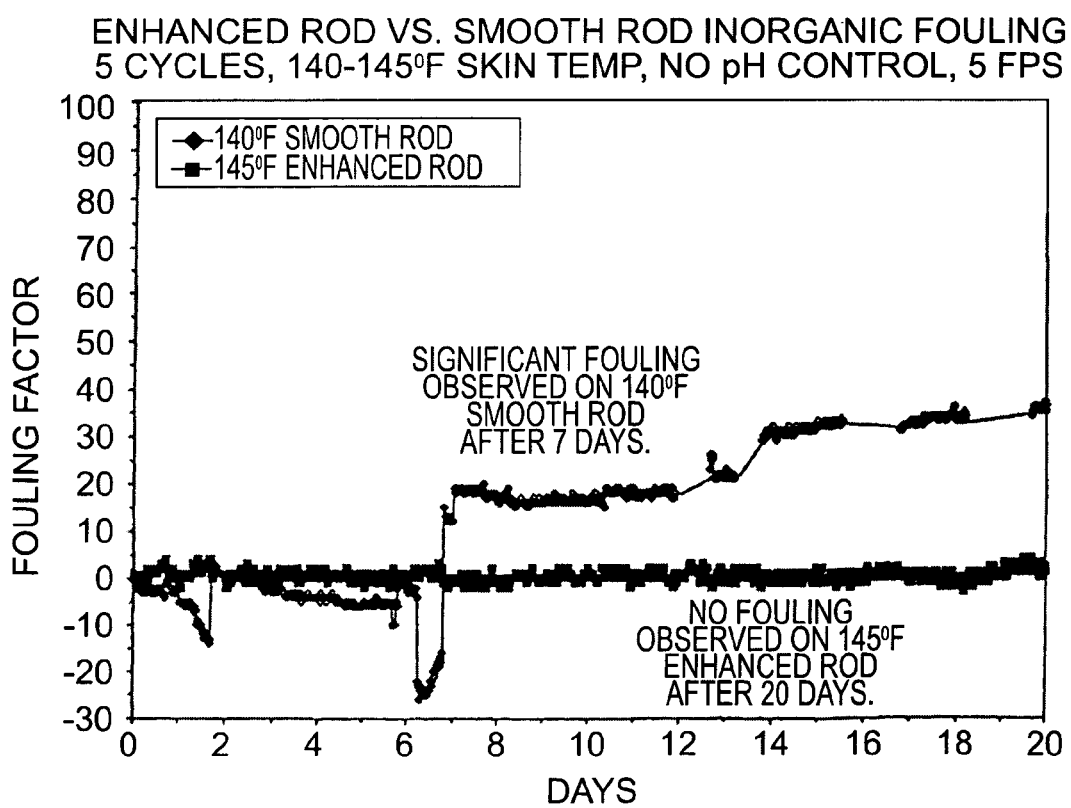

Initially, tests were conducted to determine the relative fouling tendency of enhanced tubes versus smooth tubes in the presence of inorganic foulants, such as calcium carbonate and calcium phosphate in the absence of biomass. An organic deposit and corrosion control additive blend was also present in the cooling water. The chemistry under which the tests were performed is listed in Table 2. Under those conditions, with a velocity of 1.6 m/sec. (5 ft/sec.) and a surface temperature of 65.5° C. (150° F.) on the smooth rod, fouling occurred within 7 days (standard water chemistry concentrated 5 times). At a lower surface temperature of 54.4° C. (130° F.) fouling of the smooth rod was not observed until the 14th day wherein the standard water chemistry was concentrated to 9.0 times with an additional 1.5 mg/L of orthophosphate present. The enhanced rod required an increase in skin temperature to 63° C. (145° F.) in conjunction with concentrating the standard water chemistry by a factor of 9.5 and an additional presence of 1.9 mg/L of orthophosphate. Under these conditions the enhanced rod took approximately twice as long to foul in the presence of almost double (i.e. 1.9×) the amount of inorganic impurities than the smooth rod. The results are illustrated in FIG. 5. This test was repeated with one enhanced rod (63° C.) and one smooth rod (60° C.) with the standard water chemistry concentrated to 5 cycles. The smooth rod fouled in 7 days but the enhanced rod did not foul in the 20 days when the test was terminated as illustrated in FIG. 6. Subsequent tests confirmed these results.

TABLE 2

Inorganic Crystallization Test Run Water Chemistry and Data

| Standard Water Cycled | 5 Cycles | 9 Cycles | 9.5 Cycles |
|---|---|---|---|
| pH | 8.8 | 8.8 | 8.3 |
| "P" Alkalinity, mg/L as $CaCO_3$ | 52 | 73 | 0 |
| Carbonate, mg/L as $CaCO_3$ | 104 | 146 | 0 |
| Total Alkalinity, mg/L as $CaCO_3$ | 420 | 579 | 578 |
| Bicarbonate, mg/L as $CaCO_3$ | 316 | 433 | 578 |
| Calcium Hardness, mg/L as $CaCO_3$ | 397 | 404 | 400 |
| Magnesium Hardness, mg/L as $CaCO_3$ | 265 | 575 | 628 |
| Chloride, mg/L as Cl | 354 | 639 | 697 |
| Sulfate, mg/L as $SO_4$ | 415 | 514 | 526 |
| Ortho Phosphate, mg/L as $PO_4$ | 2.5 | 4.0 | 4.4 |
| Conductivity, µS/cm² | 2340 | 4770 | 5200 |

Tube Velocity, m/sec. - 1.6
Skin Temperatures ° C. - 54.4, 62.8, 65.5
Deposit Control Additive - 150 mg/L, (12.5 mg/L active deposit control compounds)

Example 2

Organic Fouling (Biofouling)

Figure 7:
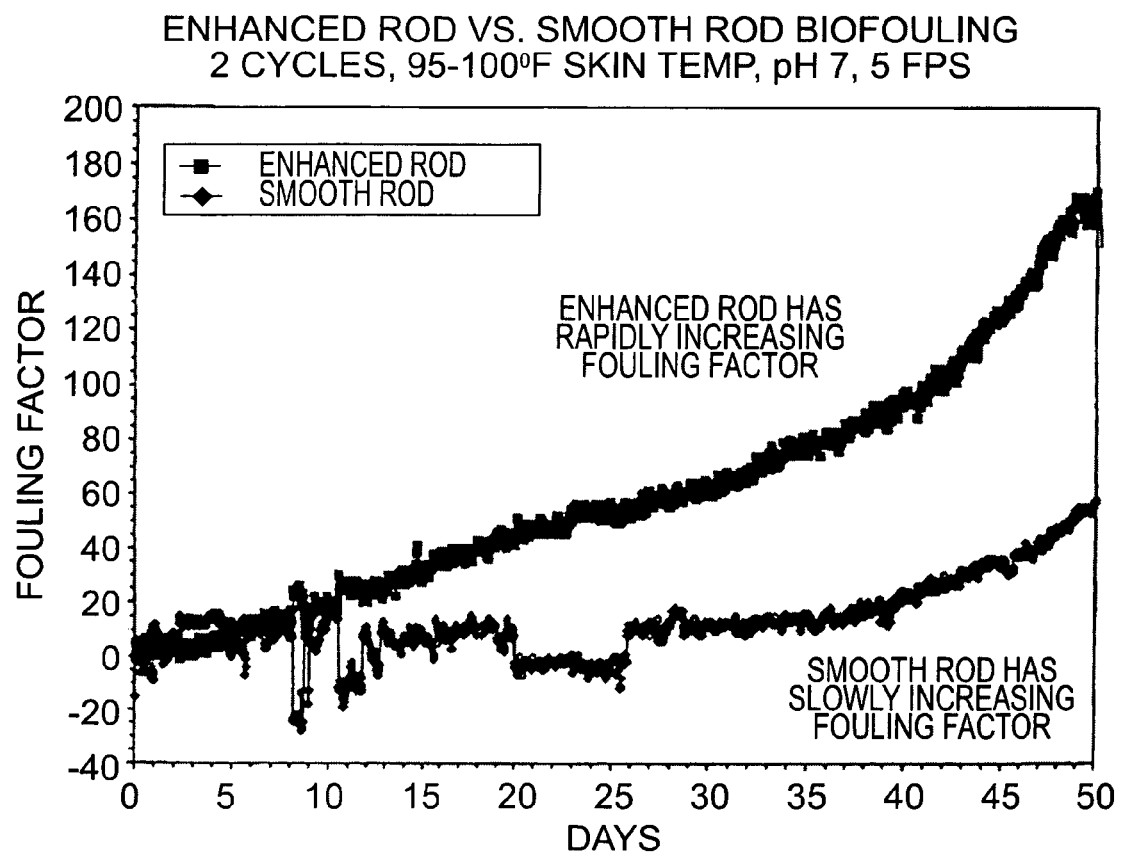

Further experiments were focused on fouling associated with biomass and to discover an efficient means to remove accumulated biomass. A blank biofouling run was performed where the cooling water was inoculated with *pseudomonas aerigenosa* (ATCC 27853), a known slime forming aerobic bacterium. Nutrient broth was added to the tower daily at a dose of 50 mg/L. Chemistry and data associated with this test run are provided in Table 3. Although biofouling was observable by the naked eye by the seventh day into the run, it was actually detected as an increasing trend on the third and fifth day by the enhanced tube and smooth tube respectively. The enhanced rod fouled at a linear rate of 0.439 $m^2$-° K/Watt-sec., while the smooth rod fouled at a rate of 0.097 $m^2$-° K/Watt-sec. as illustrated in FIG. 7.

TABLE 3

Blank Biofouling Run - Water Chemistry and Data

| | |
|---|---|
| pH | 7.0 |
| "P" Alkalinity, mg/L as $CaCO_3$ | 0 |
| Carbonate, mg/L as $CaCO_3$ | 0 |
| Total Alkalinity, mg/L as $CaCO_3$ | 54 |
| Bicarbonate, mg/L as $CaCO_3$ | 54 |
| Calcium Hardness, mg/L as $CaCO_3$ | 162 |
| Magnesium Hardness, mg/L as $CaCO_3$ | 96 |
| Chloride, mg/L as Cl | 116 |
| Sulfate, mg/L as $SO_4$ | 230 |
| Conductivity, $\mu S/cm^2$ | 936 |

Aerobic Bacteria added - *Pseudomonas aerigenosa* - 455 × $10^6$ CFU/mL
Difco Nutrient Broth (37.5% Beef Extract + 62.5% Peptone) - 50 mg/L/day
Tube velocity, m/sec - 1.6-1.68
Skin Temperature ° C. - 37.8

Example 3

Subsequent Biofouling Testing

Subsequent tests were run until the enhanced rod flutes (grooves between adjacent ribs) were filled with foulants, then various chemistries were employed to clean the rod. The smooth rod never did foul as fast as the enhanced rod, nor did it foul to the extent seen with the enhanced rod.

As illustrated by the preceding disclosure, an enhanced rod incorporated in a side stream heat transfer test section can be employed to detect fouling occurrence rapidly as well as tracking the clean-up improvements to completion. This capability can provide enhancements to performance-based monitoring control for cooling waters. If used in conjunction with a smooth bore tube monitor (i.e., a monitor with a smooth rod) in parallel, an enhanced tube monitor (i.e., a monitor with an enhanced rod) can allow for categorization of the type of foulant that is detected. Thus, the appropriate mitigation method and chemistry selection can be implemented.

The monitoring capabilities discussed above promote rapid foulant detection and characterization, and allow for proactive corrective treatment measures that can prevent excessive heat transfer losses and the development of localized corrosion. This monitoring and foulant control technology should allow for a broader acceptance and applicability of the use of enhanced tubes in the cooling water industry.

While the apparatuses and systems of the present disclosure have been described generally in the context of an aqueous heat transfer fluid circulating through a heat exchanger, it will be understood that the apparatuses and systems are applicable to any heat transfer fluid including hydrocarbons, euthetic salt solutions and the like, circulating through a vessel in heat transfer relationship where fouling is a problem. Additionally, provisions for the measurements of parameters other than corrosion, pH and conductivity, such as cation concentrations, etc. may be readily provided for in the monitoring and recording assembly.

Although the present apparatuses and systems have been described in connection with exemplary embodiments thereof, it will be understood that many modifications will be apparent to those of ordinary skill in the art; and that this application is intended to cover any adaptations or variations thereof. Therefore, it is manifestly intended that the invention be only limited by the claims and the equivalents thereof.

We claim:

1. An apparatus for monitoring and recording fouling of an aqueous system comprising:
   (a) a piping assembly integrated or coupled with a monitoring and recording assembly;
   (b) a heat transfer test assembly comprising:
      (i) an outer tube member;
      (ii) a heating rod positioned coaxially within the outer tube member, said heating rod comprising means for sensing a wall temperature of said heating rod;
      (iii) a tube sleeve assembly coaxially fitted over the heating rod within the outer tube member, wherein said tube sleeve assembly comprises a ribbed sleeve section, an upstream flow transition section positioned upstream of and butted against an upstream end of the ribbed sleeve section, and a downstream flow transition section positioned downstream of and butted against a downstream end of the ribbed sleeve section; and
      (iv) an annular fluid flow passageway disposed between the tube sleeve assembly and the outer tube member wherein the heat transfer test assembly is disposed within the piping assembly; and
   (c) an additional heat transfer test assembly disposed within the additional heat transfer test assembly comprising:
      (i) an additional outer tube member;
      (ii) an additional heating rod positioned coaxially within the outer tube member, said additional heating rod comprising means for sensing a wall temperature of said additional rod, wherein said additional heating rod comprises a smooth outer surface; and
      (iv) an annular fluid flow passageway disposed between the additional heating rod and the outer tube member.

2. The heat transfer test assembly of claim 1, wherein the outer tube member is constructed of a transparent material.

3. The heat transfer test assembly of claim 1, wherein the means of sensing the wall temperature of said heating rod comprise at least one thermocouple.

4. The heat transfer test assembly of claim 1, wherein the ribbed tube sleeve is constructed of a material selected from the group consisting of: stainless steel, copper, copper alloy, titanium and carbon steel.

5. The heat transfer test assembly of claim 1, wherein the heating rod comprises a tubular member in which a heating element is embedded within an insulating matrix.

* * * * *

UNITED STATES PATENT AND TRADEMARK OFFICE
CERTIFICATE OF CORRECTION

PATENT NO. : 7,581,874 B2  Page 1 of 1
APPLICATION NO. : 11/393943
DATED : September 1, 2009
INVENTOR(S) : George Hays It is certified that error appears in the above-identified patent and that said Letters Patent is hereby corrected as shown below:

At Column 12, line 39, insert --the piping assembly--, after "within"

At Column 12, line 47, delete "(iv)" and insert therefor --(iii)--

Signed and Sealed this

Sixteenth Day of February, 2010

David J. Kappos
*Director of the United States Patent and Trademark Office*